(12) United States Patent
Cheng et al.

(10) Patent No.: US 9,933,388 B2
(45) Date of Patent: Apr. 3, 2018

(54) INTEGRATED BIOSENSOR

(71) Applicant: Taiwan Semiconductor Manufacturing Co., Ltd., Hsin-Chu (TW)

(72) Inventors: Chun-Wen Cheng, Zhubei (TW); Fei-Lung Lai, New Taipei (TW); Chia-Hua Chu, Zhubei (TW); Yi-Hsien Chang, Shetou Township (TW); Hsin-Chieh Huang, Hsin-Chu (TW)

(73) Assignee: Taiwan Semiconductor Manufacturing Co., Ltd., Hsin-Chu (TW)

( * ) Notice: Subject to any disclaimer, the term of this patent is extended or adjusted under 35 U.S.C. 154(b) by 0 days.

(21) Appl. No.: 15/277,108

(22) Filed: Sep. 27, 2016

(65) Prior Publication Data
US 2017/0016851 A1    Jan. 19, 2017

Related U.S. Application Data

(63) Continuation of application No. 14/573,162, filed on Dec. 17, 2014, now Pat. No. 9,488,615.

(51) Int. Cl.
*G01N 27/414* (2006.01)
*H01L 21/48* (2006.01)
(Continued)

(52) U.S. Cl.
CPC ..... *G01N 27/4148* (2013.01); *G01N 27/4145* (2013.01); *H01L 21/486* (2013.01);
(Continued)

(58) Field of Classification Search
CPC ............ G01N 27/4148; H01L 21/4846; H01L 21/486; H01L 23/498; H01L 23/49811; H01L 23/49827; H01L 23/49894
See application file for complete search history.

(56) References Cited

U.S. PATENT DOCUMENTS

| 2003/0113907 A1 | 6/2003 | Roberts et al. |
| 2005/0156207 A1 | 7/2005 | Yazawa et al. |

(Continued)

OTHER PUBLICATIONS

Nakazato, Kazuo "Potentiometric, Amperometric, and Impedimetric CMOS Biosensor Array." Potentiometric, Amperometric, and Impedimetric CMOS Biosensor Array http://dx.doi.org/10.5772/53319. Published in 2013.
(Continued)

*Primary Examiner* — Peter Bradford
(74) *Attorney, Agent, or Firm* — Eschweiler & Potashnik, LLC

(57) ABSTRACT

The present disclosure relates to an integrated chip having an integrated bio-sensor with horizontal and vertical sensing surfaces. In some embodiments, the integrated chip has a sensing device disposed within a substrate, and a lower metal wire over the substrate and electrically coupled to the sensing device. First and second metal vias are arranged on the lower metal wire at locations set back from sidewalls of the lower metal wire, and first and second upper metal wires respectively cover top surfaces of the first and second metal vias. A dielectric structure surrounds the lower metal wire, the first and second metal vias, and the first and second upper metal wires. A sensing well has sensing surfaces that extend along an upper surface of the lower metal wire and along sidewalls of the first and second metal vias and the first and second upper metal wires.

20 Claims, 10 Drawing Sheets

(51) Int. Cl.
    *H01L 23/522*    (2006.01)
    *H01L 23/528*    (2006.01)
(52) U.S. Cl.
    CPC ...... *H01L 23/5226* (2013.01); *H01L 23/5283* (2013.01); *H01L 2924/0002* (2013.01)

(56) References Cited

U.S. PATENT DOCUMENTS

2013/0341734 A1   12/2013   Merz
2014/0308752 A1   10/2014   Chang et al.

OTHER PUBLICATIONS

Non-Final Office Action dated Jan. 15, 2016 for U.S. Appl. No. 14/573,162.
Final Office Action dated May 5, 2016 for U.S. Appl. No. 14/573,162.
Notice of Allowance dated Jul. 5, 2016 for U.S. Appl. No. 14/573,162.
Fusayo et al., "Electrowetting on dielectrics (EWOD): reducing voltage requirements for microfluidics." Polym. Mater. Sci. Eng 85: 12-13 (2001).

INTEGRATED BIOSENSOR

REFERENCE TO RELATED APPLICATION

This Application is a Continuation of U.S. application Ser. No. 14/573,162 filed on Dec. 17, 2014, the contents of which is hereby incorporated by reference in its entirety.

BACKGROUND

In recent years, the semiconductor industry has developed integrated chips (ICs) having integrated bio-sensors configured to detect the presence of certain biomarkers in an ambient environment (e.g., a patient's blood stream). These bio-sensors take advantage of the selective interaction and binding of certain biological receptors to identify and detect different analytes such as toxins, hormones, DNA strands, proteins, bacteria, etc., in a variety of applications such as molecular diagnostics, pathogen detection, and environmental monitoring.

BRIEF DESCRIPTION OF THE DRAWINGS

Aspects of the present disclosure are best understood from the following detailed description when read with the accompanying figures. It is noted that, in accordance with the standard practice in the industry, various features are not drawn to scale. In fact, the dimensions of the various features may be arbitrarily increased or reduced for clarity of discussion.

DETAILED DESCRIPTION

Figure 1:
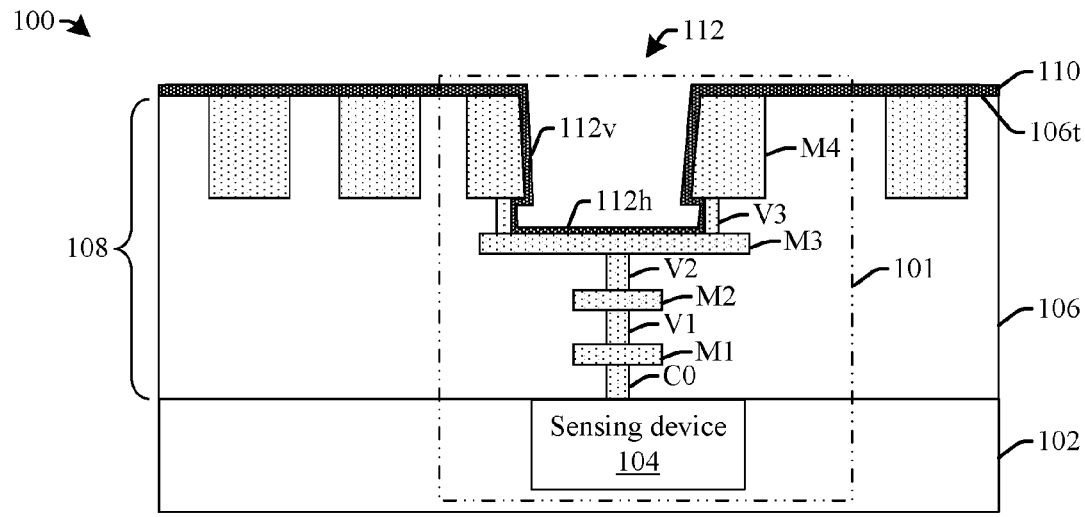
FIG. 1 illustrates some embodiments of a cross-sectional view of an integrated chip comprising an integrated bio-sensor having sensing well with horizontal and vertical sensing surfaces.

The following disclosure provides many different embodiments, or examples, for implementing different features of the provided subject matter. Specific examples of components and arrangements are described below to simplify the present disclosure. These are, of course, merely examples and are not intended to be limiting. For example, the formation of a first feature over or on a second feature in the description that follows may include embodiments in which the first and second features are formed in direct contact, and may also include embodiments in which additional features may be formed between the first and second features, such that the first and second features may not be in direct contact. In addition, the present disclosure may repeat reference numerals and/or letters in the various examples. This repetition is for the purpose of simplicity and clarity and does not in itself dictate a relationship between the various embodiments and/or configurations discussed.

Further, spatially relative terms, such as "beneath," "below," "lower," "above," "upper" and the like, may be used herein for ease of description to describe one element or feature's relationship to another element(s) or feature(s) as illustrated in the figures. The spatially relative terms are intended to encompass different orientations of the device in use or operation in addition to the orientation depicted in the figures. The apparatus may be otherwise oriented (rotated 90 degrees or at other orientations) and the spatially relative descriptors used herein may likewise be interpreted accordingly.

Integrated bio-sensors typically comprise a conductive horizontal sensing surface that is disposed within a top metal interconnect layer of an integrated chip back-end-of-the-line (BEOL) metal stack, and which is electrically coupled to a sensing device disposed within an underlying semiconductor body. A polymer material is disposed over the top metal interconnect layer to form a sensing well configured to act as a receptacle for a liquid to be analyzed. During operation, analytes from the liquid will vary electrical operation of the sensing device, indicating a presence of the analyte in the liquid.

It has been appreciated that the sensitivity of an integrated bio-sensor is proportionate to the surface area of the conductive sensing surface. However, the flat geometry of a horizontal sensing surface practically limits the size of the surface area (e.g., since the high cost of silicon real estate on a wafer limits a size of an integrated bio-sensor), thereby limiting the ability of an integrated bio-sensor to detect an analyte.

Accordingly, the present disclosure relates to an integrated chip comprising an integrated bio-sensor having horizontal and vertical sensing surfaces. In some embodiments, the integrated chip comprises a sensing device disposed within a semiconductor substrate. A back-end-of the line (BEOL) metallization stack comprising a plurality of metal interconnect layers electrically coupled to the sensing device is disposed within an inter-level dielectric (ILD) layer overlying the semiconductor substrate. A sensing well is located within a top surface of the ILD layer. The sensing well comprises a horizontal sensing surface extending along a top surface of a first one of the plurality of metal interconnect layers and a vertical sensing surface extending along a sidewall of a second one of the plurality of metal interconnect layers overlying the first one of the plurality of metal interconnect layers. The use of both horizontal and vertical sensing surfaces increases the total area of the sensing surface. The increased sensing area enables more accurate sensing (e.g., high sensitivity and high signal response), and can also provide for an optimum ratio of a sensing surface to a volume of the sensing well for detection of specific analytes (i.e., bio-targets).

FIG. 1 illustrates some embodiments of a cross-sectional view of an integrated chip 100 comprising an integrated bio-sensor 101 having a sensing well with horizontal and vertical sensing surfaces.

The integrated bio-sensor 101 comprises a sensing device 104 disposed within a semiconductor substrate 102. The sensing device 104 is electrically coupled to a back-end-of-the-line (BEOL) metallization stack 108 comprising a plurality of metal interconnect layers, C0-M4, disposed within an inter-level dielectric (ILD) layer 106 having one or more dielectric materials. In some embodiments, the BEOL metallization stack 108 may comprise a conductive contact C0 configured to connect the sensing device C0 to one or more overlying metal wires Mx (x=1, 2, 3, 4) vertically interconnected by way of one or more metal vias Vx (x=1, 2, 3). In some embodiments, the conductive contact C0 and the metal vias Vx may comprise tungsten or copper, while the metal wire Mx may comprise copper or aluminum.

The ILD layer 106 comprises a sensing well 112 disposed within a top surface 106t of the ILD layer 106. The sensing well 112 comprises a cavity or negative relief within the top surface 106t of the ILD layer 106. A sensing enhancement layer 110 is disposed onto interior surfaces of the sensing well 112. In some embodiments, the sensing enhancement layer 110 may also extend along the top surface 106t of the ILD layer 106. The sensing enhancement layer 110 may comprise a high-k dielectric layer configured to enhance electrical interaction between analytes within a sample (e.g., a liquid) and the plurality of metal interconnect layers, C0-M4.

The sensing well 112 comprises a horizontal sensing surface 112h and one or more vertical sensing surfaces 112v. The horizontal sensing surface 112h runs along a middle metal wire layer M3 (i.e., a metal wire layer having overlying metal layers) extending in a lateral direction within the BEOL metallization stack 108. The one or more vertical sensing surfaces 112v run along sidewalls of one or more overlying metal interconnect layers, V3 and M4, within the BEOL metallization stack 108. For example, metal wire layer M3 runs along a bottom surface of the sensing well 112 to form a horizontal sensing surface 112h, while metal via layer V3 and overlying metal wire layer M4 run along one or more sidewalls of the sensing well 112 to form vertical sensing surfaces 112v.

The use of the vertical sensing surfaces 112v, in addition to the horizontal sensing surface 112h, increases the total area of the sensing surface relative to bio-sensors that do not have vertical sensing surfaces. The increased sensing area gives more chance for the integrated bio-sensor 101 to sense an analyte (i.e., to generate more charge from ions, photons, or any charge inducted sources in an liquid), thereby enabling more accurate sensing (e.g., high sensitivity and high signal response).

Figure 2A:
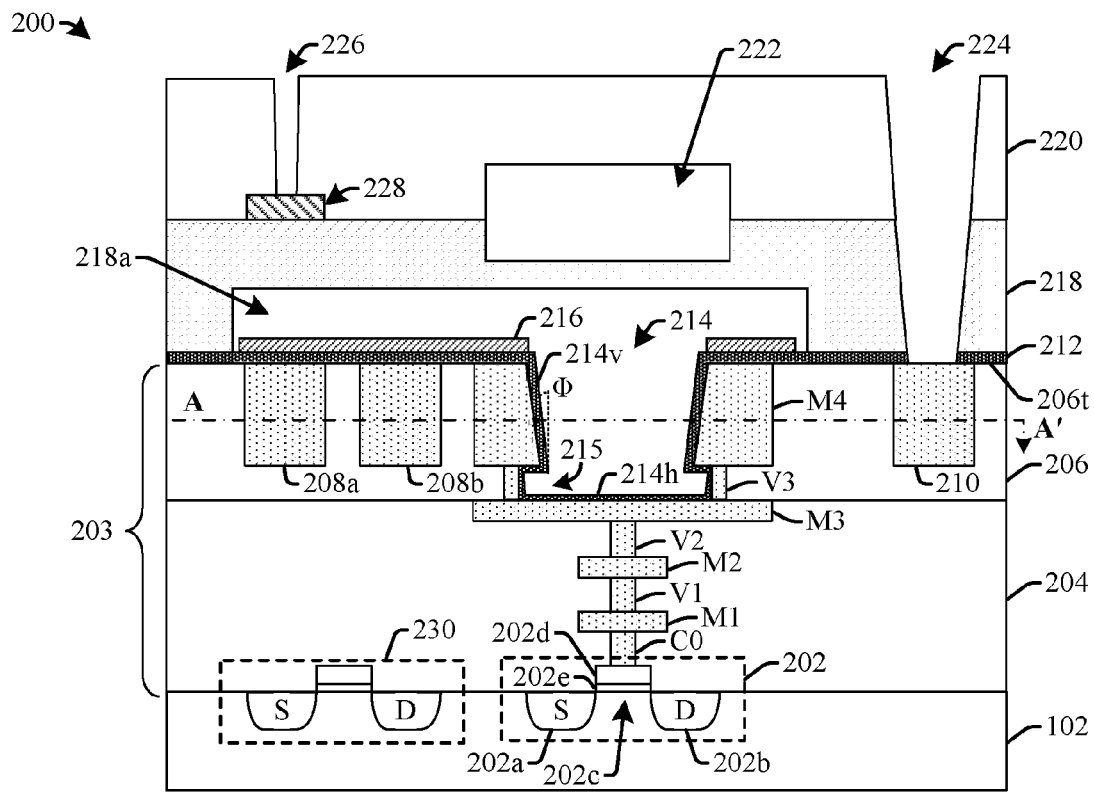
FIGS. 2A-2B illustrate some alternative embodiments of an integrated chip comprising an integrated bio-sensor having sensing well with horizontal and vertical sensing surfaces.
Figure 2B:
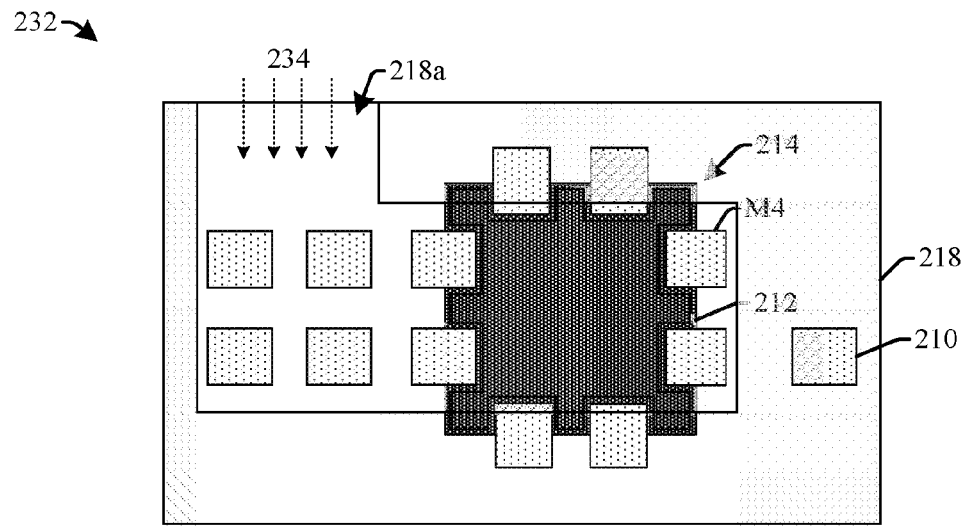

FIGS. 2a-2b illustrate some alternative embodiments of an integrated chip 200 comprising an integrated bio-sensor having a sensing well 214 with horizontal and vertical sensing surfaces.

As shown in FIG. 2a, the integrated chip 200 comprises a sensing device 202 disposed within a semiconductor substrate 102. In some embodiments, the sensing device 202 may comprise a MOSFET device having a source region 202a and a drain region 202b laterally separated by a channel region 202c. A gate region 202d is vertically separated from the channel region 202c by way of a gate dielectric layer 202e (e.g., a silicon dioxide ($SiO_2$) layer).

The gate region 202d of the semiconductor device is electrically coupled to one or more lower metal layers C0-V2, disposed within a first ILD material 204 in a BEOL metallization stack 203. In some embodiments, the first ILD material 204 may comprise one or more different ILD layers. A middle metal wire layer M3 is disposed over and is connected to the one or more lower metal layers C0-V2. In various embodiments, the middle metal wire layer M3 may be disposed within the first ILD material 204 or within a different, second ILD material 206 overlying the first ILD material 204. One or more upper metal layers V3-M4 are disposed over and are electrically connected to the middle metal wire layer M3. In some embodiments, the one or more upper metal layers V3-M4 may be disposed within the second ILD material 206. In various embodiments, the first ILD material 204 and the second ILD material 206 may comprise a same dielectric material or different dielectric materials. For example, in some embodiments, the lower one or more lower metal layers C0-V2 may comprise thin metal layers disposed within a low-k or an extreme low-k dielectric material, while the middle and/or upper metal layers M2 and/or V3-M4 may comprise a thicker metal layers disposed within a silicon dioxide ($SiO_2$) layer.

A sensing well 214 is disposed within a top surface 206t of the second ILD material 206. The sensing well 214 extends from the top surface 206t of the second ILD material 206 to a top surface of the middle metal wire layer M3. The middle metal wire layer M3 and the upper metal layers V3-M4 abutting the sensing well 214 are electrically coupled to the gate region 202d, so as to form an extended gate electrode. The sensing device 202 is able to detect analytes (e.g., ion concentrations, photon concentrations, DNA sequences, etc.) based upon changes in electric potential change around the extended gate electrode (e.g., based upon a change in electric charge around the extended gate electrode determined by Poisson's equal or based upon a chemical equilibrium potential determined by the Nernest equation).

In some embodiments, a sensing enhancement layer 212 comprising a high-k dielectric material is disposed onto interior surfaces of the sensing well 214. For example, the sensing enhancement layer 212 may be disposed onto a horizontal sensing surface 214h running along a bottom surface of the sensing well 214 and a vertical sensing surface 214v running along sidewalls of the sensing well 214. In some embodiments, the sensing enhancement layer 212 may have thicknesses in a range of between approximately 10 angstroms and approximately 200 angstroms along the horizontal and vertical sensing surfaces, 214h and 214v. In some embodiments, the sensing enhancement layer 212 may also extend along the top surface 206t of the second ILD material 206. In various embodiments, the sensing enhancement layer 212 may comprise one or more of silicon nitride ($Si_3N_4$), aluminum oxide ($Al_2O_3$), titanium oxide ($TiO_2$), hafnium oxide ($HfO_2$), tantalum pentoxide ($Ta_2O_5$), tin oxide (SnO), tin dioxide ($SnO_2$), $BaxSr_1\text{-}xTiO_3$ (BST).

In some embodiments, the sensing well 214 may vertically extend along a via layer V3 and an overlying upper metal wire layer M4. In some embodiments, the sensing well 214 is disposed between two or more vias of a via array and metal wires within the upper metal layers V3-M4. In some such embodiments, the sidewalls of the sensing well 214 may comprise angled sidewalls (e.g., sidewalls having an angle Φ with respect to a normal) along the upper metal wire layer M4. In some embodiments, the sensing well 214 may comprise nooks 215 disposed within the sidewalls of the sensing well 214 at a position vertically underlying the upper metal wire layer M4.

A first capping structure 218 and a second capping structure 220 may be disposed over the semiconductor substrate 102. In some embodiments, the first capping structure 218 may be bonded to the second ILD layer 206 by way of a first adhesive layer and the second capping structure 220 may be bonded to the first capping structure 218 by way of a second adhesive layer. In some embodiments, the first capping structure 218 comprises a malleable polymer material, while the second capping structure 220 may comprise a rigid material. For example, in some embodiments, the first capping structure 218 may comprise PDMS (polydimethylsiloxane), while the second capping structure 220 may comprise quartz. In other embodiments, the first and/or second capping structures, 218 and 220, may comprise quartz and/or silicon. In some embodiments, the first capping structure 218 and second capping structure 220 may be optically transmissive (i.e., transparent). In such embodiments, reactions occurring within the sensing well 214 may be optically observed (e.g., using a microscope external to the integrated chip 200).

In some embodiments, a first side of the first capping structure 218 facing the semiconductor substrate 102 may comprise a first cavity and a second side of the first capping structure 218 opposing the semiconductor substrate 102 may comprise a second cavity. The first cavity forms a micro-fluidic channel 218a over the second ILD material 206, which extends over the sensing well 214. The second cavity may form a chamber 222, which may be expanded to operate as a peristaltic pump and/or valve. For example, if the pressure in the chamber 222 is increased, the bottom wall of the chamber 222 will move downward, either acting as a valve (to block liquid from entering the sensing well 214) or a pump (to push liquid into the sensing well 214).

In some embodiments, the upper metal wire layer M4 may comprise one or more EWOD (electrowetting on dielectrics) electrodes, 208a and 208b. In some embodiments, a hydrophobic layer 216 is disposed over the sensing enhancement layer 212 at a position overlying the EWOD electrodes, 208a and 208b. In some embodiments, the hydrophobic layer 216 may comprise a self assembled monolayer (SAM) or a teflon material. The EWOD electrodes, 208a and 208b, are configured to selectively generate electric fields that are configured to modify wetting properties of the hydrophobic layer 216 to control the flow of liquid within the micro-fluidic channel 218a. For example, the EWOD electrodes, 208a and 208b, may be configured to manipulate liquid drops in a manner that fills the sensing well 214. In other embodiments, the integrated chip 200 may comprise alternative droplet manipulation elements, such as light-generation elements that enable droplet manipulation by optical tweezers or electrodes that generate non-uniform electric fields to enable droplet manipulation by dielecrophoresis.

In some embodiments, the integrated chip 200 may further comprise a heating element 230. In some embodiments, the heating element 230 may be disposed within the semiconductor substrate 102. The heating element 230 may be configured to vary a temperature of a liquid within the micro-fluidic channel 218a that is to be sampled by the sensing well 214 to enable a desired reaction within the liquid (e.g., to amplify a DNA signal by changing DNA from a double strand structure to a single strand structure). In some embodiments, a temperature sensor 228 may be disposed between the second and third capping structures, 218 and 220. In some embodiments, the temperature sensor 228 may comprise a thermal coupling element (e.g., a platinum thermocouple).

In some embodiment, the second capping structure 220 may have a first opening 224 and a second opening 226. The first opening 224 extends through the second capping structure 220 and the underlying first capping structure 218 to an underlying signal output electrode 210 within the upper metal layer M4. The first opening 224 provides an opening in which an electrical connection can be made from the integrated bio-sensor (e.g., from signal output electrode 210) to an external circuit. The second opening 226 exposes the temperature sensor 228 to an ambient environment, thereby allowing the temperature sensor 228 to measure a temperature of a liquid in the ambient environment. In some embodiments, the heating element 230 is configured to generate heat dependent upon a temperature measured by the temperature sensor 228. For example, if the temperature sensor 228 measures a first temperature of the ambient environment the heating element 230 may be operated to generate a first amount of heat, while if the temperature sensor 228 measures a second temperature less than the first temperature the heating element 230 may be operated to generate a second amount of heat greater than the first amount of heat.

FIG. 2b illustrates some embodiments of a top-view 232 of the integrated chip 200 (along line A-A' of FIG. 2a). As shown in top-view 232, the upper metal wire layers V3-M4 are arranged along opposing sides of the sensing well 214. By arranging the upper metal wire layer M4 along opposing sides of the sensing well 214, the total surface area of the sensing area can be increased to thereby provide for more accurate sensing. The micro-fluidic channel 218a provides a path between an ambient environment to the sensing well 214, which provides a sample 234 to the sensing well 214. While top-view 232 illustrates the integrated bio-sensor 200 as comprises a sensing well 214 having a substantially square shape, it will be appreciated that in other embodiments, the sensing well 214 may have alternative shapes (e.g., a circular shape, an oblong shape, a triangular shape, etc.). Furthermore, while the micro-fluidic channel is illustrated as providing a path from a side of the semiconductor substrate 102 to the sensing well 214, it will be appreciated that the channel may alternatively provide a path from a top of a capping structure, 218 or 220, to the sensing well 214.

Figure 3A:
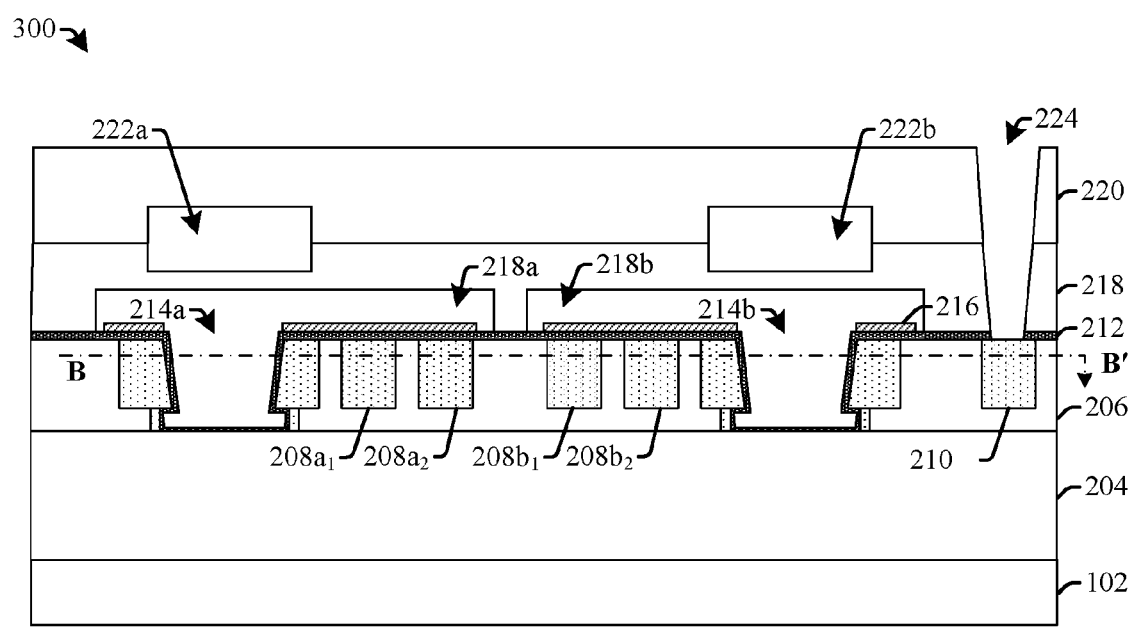
FIGS. 3A-3B illustrates some embodiments of an integrated chip comprising an array of sensing wells that is operable to detect different analytes.
Figure 3B:
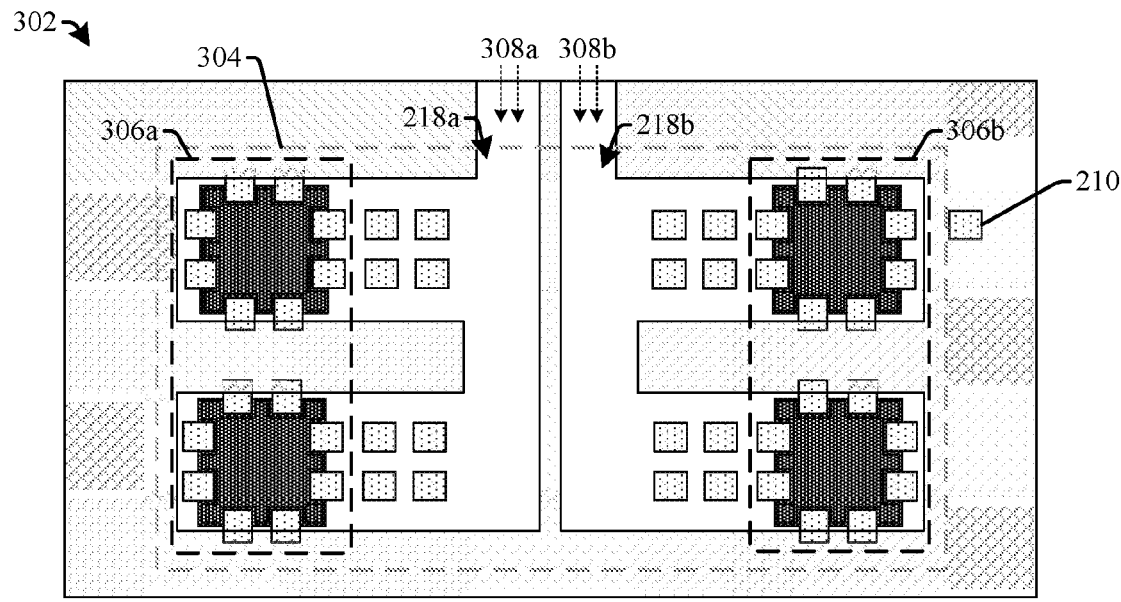

FIGS. 3a-3b illustrates some embodiments of an integrated chip comprising an array of sensing wells that is operable to detect different analytes.

FIG. 3a illustrates a cross-sectional view of some alternative embodiments of an integrated chip 300 comprising an array of sensing wells having a plurality of sensing wells, 214a and 214b. The plurality of sensing wells, 214a and 214b, are coupled to one or more micro-fluidic channels, 218a and 218b, which are configured to perform a multiplexing operation that provides a liquid to a first one of the sensing wells, 214a or 214b, without providing the liquid to a second one of the sensing wells, 214b or 214a. In some embodiments, cavities 222a or 222b may act as a valve to prevent liquid from being provided one of the sensing wells, 214a or 214b.

FIG. 3b illustrates a top-view 302 corresponding to integrated chip 300 (along line B-B' of FIG. 3a). As shown in top-view 302, the micro-fluidic channels, 218a and 218b, separate the array of sensing wells 304 into first and second sub-arrays, 306a and 306b. By using the micro-fluidic channels, 218a and 218b, to provide liquid to different sub-arrays, 306a or 306b, of sensing wells, the integrated chip 300 is able to perform multiplexing that enables the integrated chip 300 to detect different analytes. For example, during operation, a first biologically sensitive element such as a first enzyme 308a may be introduced into sensing wells of the first sub-array 306a by way of micro-fluidic channel 218a. The first enzyme 308a is immobilized onto the sensing enhancement layer of sensing wells of the first sub-array 306a, thereby enabling the first sub-array 306a to detect a first analyte associated with the first enzyme 308a. Similarly, a second biologically sensitive element such as a second enzyme 308b may be introduced into sensing wells of the second sub-array 306a by way of micro-fluidic channel 218b. The second enzyme 308b is immobilized onto the sensing enhancement layer of sensing wells of the second sub-array 306b, thereby enabling the second sub-array 306b to detect a second analyte (different than the first analyte) corresponding to the second enzyme 308b.

Figure 4:
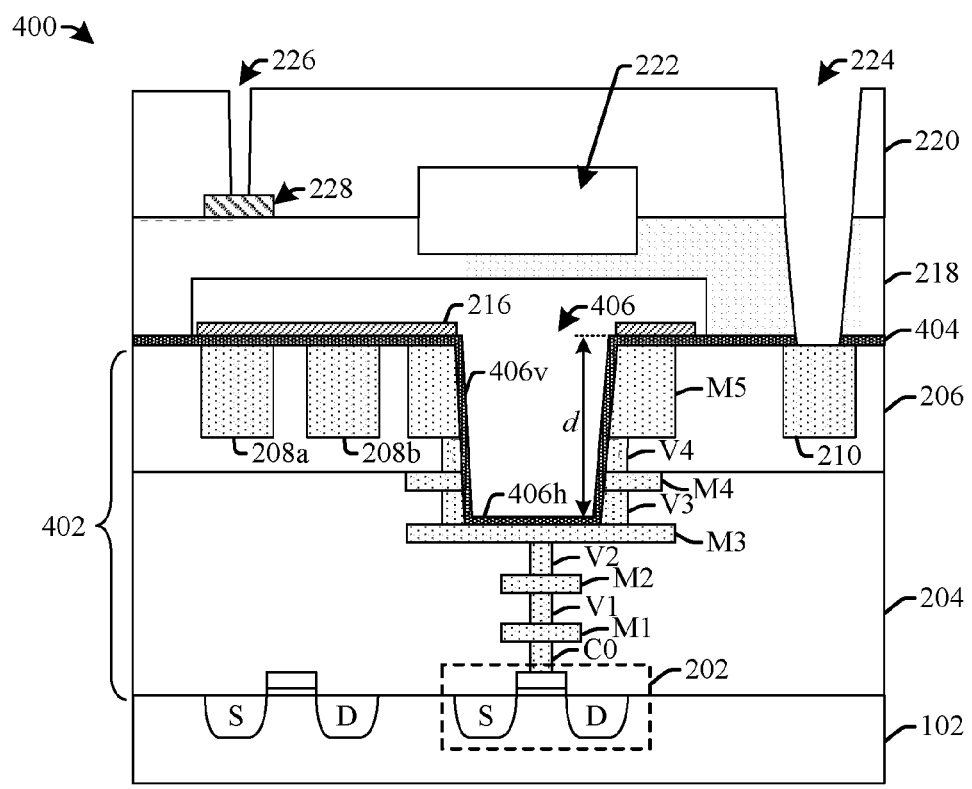
FIGS. 4-8 illustrate some alternative embodiments of cross-sectional views of an integrated chip comprising an integrated bio-sensor having sensing well with horizontal and vertical sensing surfaces.

FIG. 4 illustrates some embodiments of a cross-sectional view of an integrated chip 300 comprising a disclosed integrated bio-sensor.

Integrated chip 400 comprises a sensing well 406 disposed within a top surface of the second ILD material 206. A sensing enhancement layer 404 is arranged on a horizontal sensing surface 406h running along a bottom of the sensing well 406 and vertical sensing surfaces 406v running along sidewalls of the sensing well 406. The vertical sensing surfaces 406v vertically extend along multiple via layers V3, V4 and metal wire layers M3, M4 of BEOL metal stack 402. For example, the sensing well 406 has sidewalls that vertically extend along first via layer V3, a second metal layer M4, a second via layer V4 and a second metal layer M5. By extending the sidewalls of the sensing well 406 along multiple via (e.g., V3 and V4) and metal wire layers (e.g., M4 and M5), a depth d of sensing well 214 can be adjusted to improve sensing accuracy and/or to provide an optimum sensing surface to volume ratio for detection of a specific analyte (e.g., bio-target). In alternative embodiments, more or less metal layers can be added to achieve the optimum ratio. In some embodiments, the sensing enhancement layer 406 may have a thickness in a range of between approximately 10 angstroms and approximately 200 angstroms along the horizontal and vertical sensing surfaces, 406h and 406v. It will be appreciated that sensing enhancement layers of subsequent figures (e.g., sensing enhancement layers 504, 604, 702, 802) may have thicknesses in a substantially same range.

Figure 5:
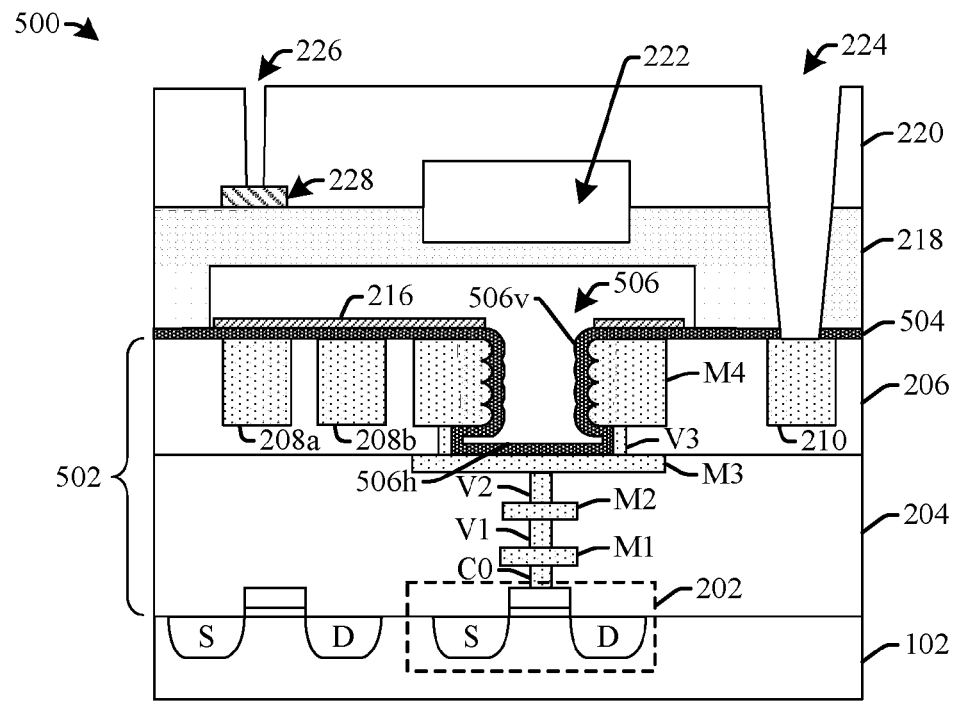

FIG. 5 illustrates some embodiments of a cross-sectional view of an integrated chip 500 comprising a disclosed integrated bio-sensor.

Figure 6:
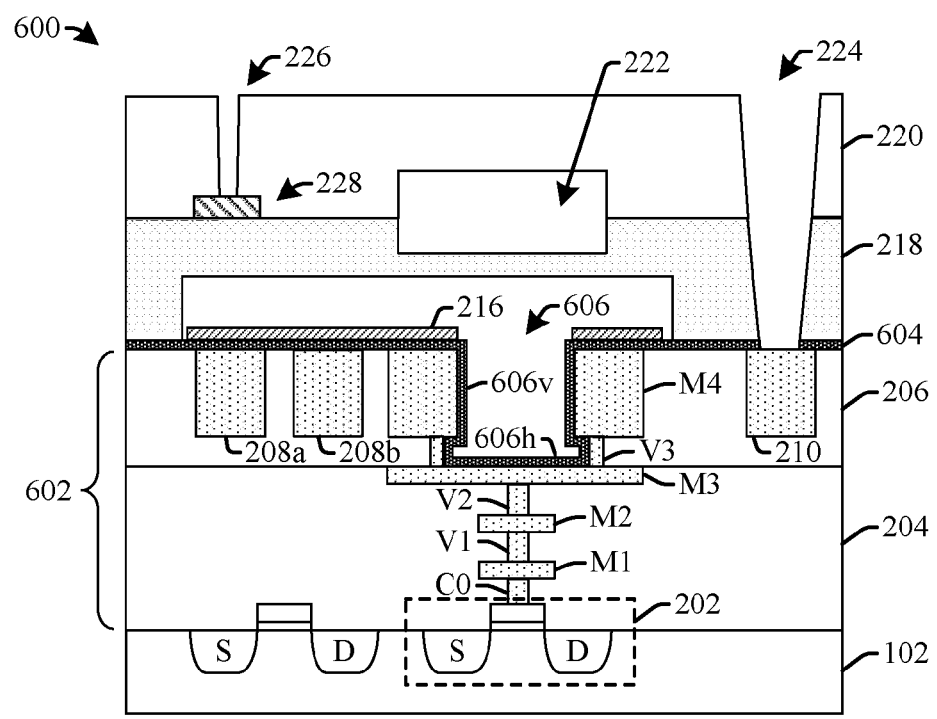

Integrated chip 500 comprises a sensing well 506 disposed within a top surface of the second ILD material 206. A sensing enhancement layer 504 may be arranged along a horizontal sensing surface 504h running along a bottom of the sensing well 506 and vertical sensing surfaces 504v running along sidewalls of the sensing well 506. The sensing enhancement layer 504 may have curved surfaces along the vertical sensing surfaces 504v, which vertically extend along multiple via layers V3, V4 and metal wire layers M3, M4 of BEOL metal stack 502. In some embodiments, the curved surfaces of the vertical sensing surfaces 506v comprises one or more arches. The arches of the vertical sensing surfaces 506v increase the surface area of the vertical sensing surfaces 506v, thereby increasing sensing area (and therefore increase the sensing signal) without substantially increasing the size of the bio-sensor. FIG. 6 illustrates some embodiments of a cross-sectional view of an integrated chip 600 comprising a disclosed integrated bio-sensor.

Integrated chip 600 comprises a sensing well 606 disposed within a top surface of the second ILD material 206. A sensing enhancement layer 604 is disposed along substantially vertical sidewalls (vertical sensing surfaces 606v) of the sensing well 606 and along a horizontal sensing surface 606h. The vertical sidewalls are perpendicular to a top surface of the semiconductor substrate 102. The substantially vertical sidewalls extend along multiple via layers V3, V4 and metal wire layers M3, M4 of BEOL metal stack 602.

Figure 7:
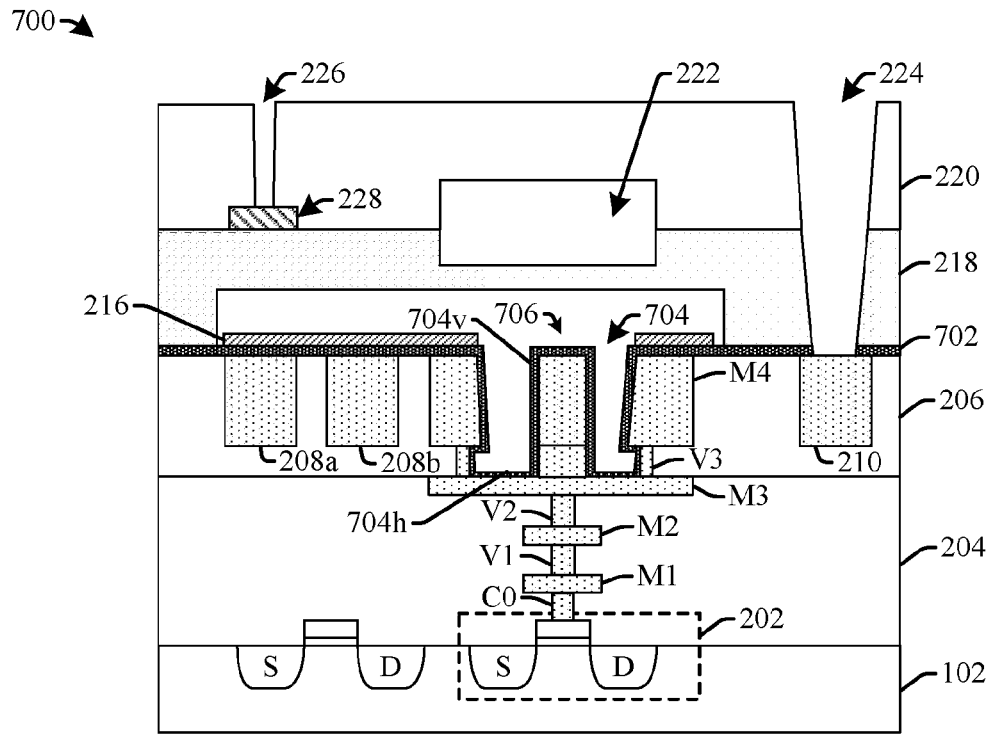

FIG. 7 illustrates some embodiments of a cross-sectional view of an integrated chip 700 comprising a disclosed integrated bio-sensor.

Integrated chip 700 comprises a sensing well 704 disposed within a top surface of the second ILD material 206. A post 706 is disposed within the sensing well 704 at a position that is laterally disposed between sidewalls of the sensing well 704. The post 706 comprises one or more metallization layers that are electrically coupled to the horizontal sensing surface (i.e., M3) and that extend into the sensing well 704 in a direction perpendicular to the horizontal sensing 704h surface to increase a total size of vertical sensing surfaces 704v. For example, the post 706 may comprise a via layer V3 and a metal layer M4 that extend into the sensing well 704. The post 706 may be surrounded by a high-k dielectric layer 702, in some embodiments.

Figure 8:
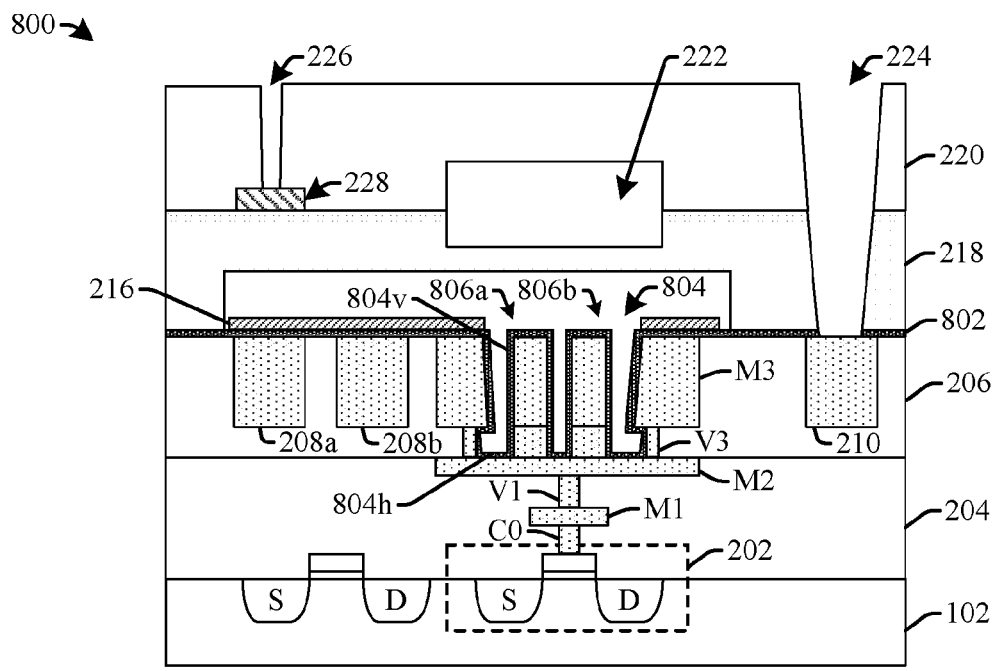

Although integrated chip 700 is illustrated as having a single post 706 extending into the sensing well 704, it will be appreciated that in other embodiments additional posts may be disposed within the sensing well 704 to further increase the sensing area (e.g., a total size of vertical sensing surfaces 704v). For example, FIG. 8 illustrates some embodiments of a cross-sectional view of an integrated chip 800 comprising a disclosed integrated bio-sensor with a sensing well 804 having a plurality of posts, 806a and 806b. The plurality of posts, 806a and 806b, may be surrounded by a high-k dielectric layer 802, in some embodiments.

Figure 9:
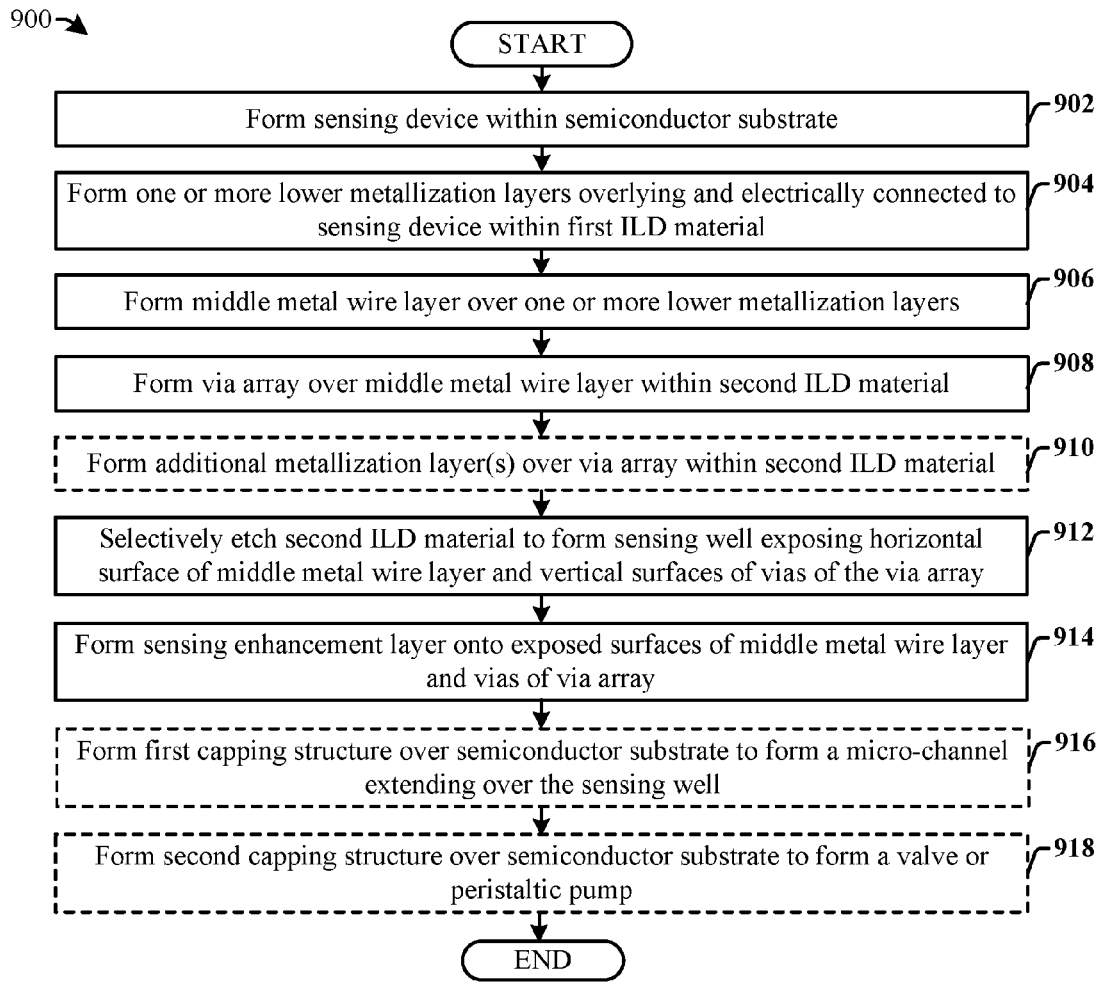
FIG. 9 illustrates a flow diagram of some embodiments of a method of forming an integrated chip comprising an integrated bio-sensor having sensing well with horizontal and vertical sensing surfaces.

FIG. 9 illustrates a flow diagram of some embodiments of a method 900 of forming an integrated chip comprising an integrated biosensor having a sensing well with horizontal and vertical sensing surfaces.

While disclosed method 900 is illustrated and described herein as a series of acts or events, it will be appreciated that the illustrated ordering of such acts or events are not to be interpreted in a limiting sense. For example, some acts may occur in different orders and/or concurrently with other acts or events apart from those illustrated and/or described herein. In addition, not all illustrated acts may be required to implement one or more aspects or embodiments of the description herein. Further, one or more of the acts depicted herein may be carried out in one or more separate acts and/or phases.

At 902, a sensing device is formed within a semiconductor substrate. In some embodiments, the sensing device may comprise a transistor device, such as a MOS transistor, for example.

At 904, one or more lower metallization layers are formed within a first inter-level dielectric (ILD) layer. The one or more lower metallization layers are overlying and electrically connected to the sensing device. In various embodiments, the one or more lower metallization layers may comprise metal wires, contacts, and/or vias.

At 906, a middle metal wire layer is formed over the lower one or more metallization layers within the first ILD material or within a second ILD material.

At 908, a via array is formed within a second ILD material over the middle metal wire layer.

At 910, one or more additional metallization layers may be formed within the second ILD material over one or more elements of the via array.

At 912, the second ILD is selectively etched to form a sensing well that exposes a horizontal surface of the middle metal wire layer and vertical surfaces of two or more vias of the via array.

At 914, a sensing enhancement layer is formed onto exposed surfaces of the middle metal wire layer and two or more vias of the via array. In some embodiments, the sensing enhancement layer may comprise a high-k dielectric layer.

At 916, a first capping structure may be formed over the semiconductor substrate. The first capping structure comprises a first cavity, within a first side facing the semiconductor substrate, which forms a micro-fluidic channel extending over the sensing well.

At 918, a second capping structure may be formed over the semiconductor substrate. The second the second capping structure has a third cavity, facing the first capping structure, which forms a valve or peristaltic pump.

FIGS. 10-17 illustrate some embodiments of cross-sectional views showing a method of forming an integrated chip comprising an integrated biosensor having sensing well with horizontal and vertical sensing surfaces. Although FIGS. 10-17 are described in relation to method 900, it will be appreciated that the structures disclosed in FIGS. 10-17 are not limited to such a method, but instead may stand alone as structures independent of the method.

Figure 10:
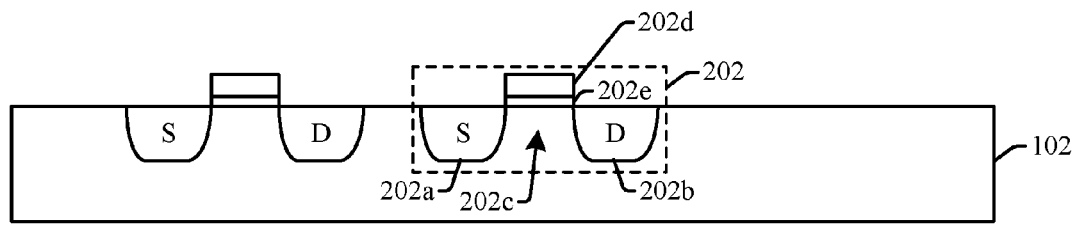
FIGS. 10-17 illustrate some embodiments of cross-sectional views showing a method of forming an integrated chip comprising an integrated bio-sensor having sensing well with horizontal and vertical sensing surfaces.

FIG. 10 illustrates some embodiments of a cross-sectional view 1000 of an integrated chip corresponding to act 902.

As shown in cross-sectional view 1000, a sensing device 202 is formed within a semiconductor substrate 102. The semiconductor substrate 102 may comprise any type of semiconductor body (e.g., silicon, SiGe, SOI) such as a semiconductor wafer and/or one or more die on a wafer, as well as any other type of semiconductor and/or epitaxial layers associated therewith. In some embodiments, the sensing device 202 comprises a MOSFET transistor having a source region 202a, a drain region 202b that is separated from the source region 202a by a channel region 202c, and a gate region 202d separated from the channel region 202c by a gate dielectric layer 202e.

Figure 11:
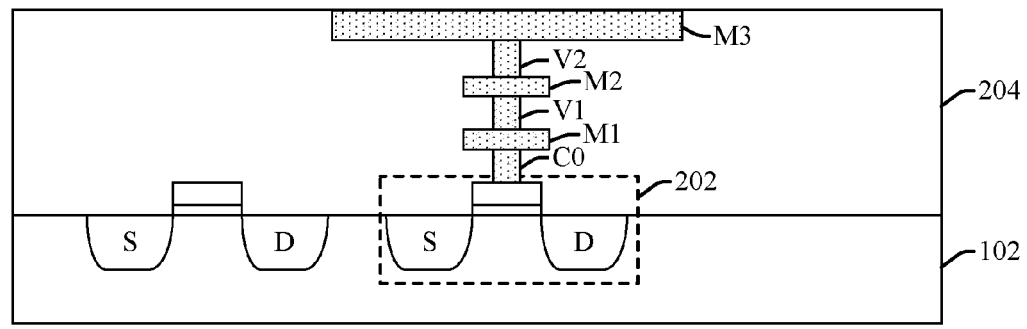

FIG. 11 illustrates a cross-sectional view 1100 of an integrated chip corresponding to acts 904-906.

As shown in cross-sectional view 1100, a first ILD material 204 is formed over the semiconductor substrate 102. The first ILD material 204 may comprise a low-k dielectric layer deposited by way of a vapor deposition technique (e.g., physical vapor deposition, chemical vapor deposition, etc.). One or more lower metallization layers C0-V2 are formed within a first ILD material 204 at a position overlying and electrically connected to the sensing device 202. The one or more lower metallization layers C0-V2 may comprise one or more metal wire layers, M1 and M2, configured to provide lateral interconnections or one or more metal via layers, V1 and V2, configured to provide vertical interconnections. In some embodiments, the one or more lower metallization layers C0-V2 may comprise tungsten and/or copper, for example. A middle metal layer M3 is subsequently formed over the one or more lower metallization layers C0-V2.

In some embodiments, the one or more lower metallization layers C0-V2 and the middle metal wire layer M3 may be formed by selectively exposing the first ILD material 204 to a first etchant, which is configured to selectively etch the first ILD material 204 to form a first plurality of openings. A metal material (e.g., tungsten or copper) is subsequently formed within the first plurality of openings. In some embodiments, the first etchant may comprise a dry etchant have an etching chemistry comprising a fluorine species (e.g., $CF_4$, $CHF_3$, $C_4F_8$, etc.). In some embodiments, the etching chemistry may further comprise oxygen or hydrogen, for example. In other embodiments, the first etchant may comprise a wet etchant comprising hydroflouric acid (HF).

In some embodiments, the one or more lower metallization layers C0-V2 and the middle metal wire layer M3 may be formed using a dual damascene process. In such embodiments, a first layer of the first ILD material 204 is deposited onto the surface of a semiconductor substrate 102. The first layer of the first ILD material 204 is then selectively etched to form a via hole and an overlying metal wire trench. After the via hole and metal wire trench are formed, a diffusion barrier layer and a seed layer are deposited within the via hole and metal wire trench. A plating (e.g., electro chemical plating) process may then be used to fill the via hole and metal line trench with metal (e.g., copper). The top surface of the first layer of the first ILD material 204 is planarized using a chemical mechanical polishing (CMP) process to remove any excess metal.

In other embodiments, the one or more lower metallization layers C0-V2 and the middle metal wire layer M3 may be formed using a single damascene process. In such embodiments, a first layer of the first ILD material 204 is selectively etched to form via holes, which are subsequently filled with a metal material (e.g., using an electro-chemical plating process). A second layer of the first ILD material 204 is then formed over the first layer. The second layer is selectively etched to form metal wire trenches, which are subsequently filled with a metal material (e.g., using an electro-chemical plating process).

Figure 12:
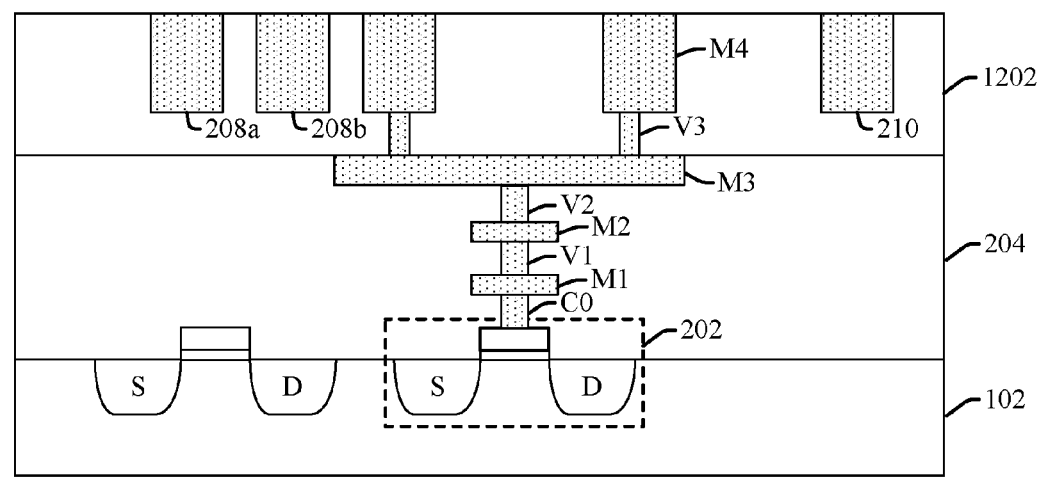

FIG. 12 illustrates a cross-sectional view 1200 of an integrated chip corresponding to acts 908-910.

As shown in cross-sectional view 1200, a via array is formed within a second inter-level dielectric (ILD) material. The via array comprises a plurality of vias V3 abutting the middle metal layer M3. In some embodiments, one or more additional metal layer may be formed over the plurality of vias V3.

In some embodiments, the second ILD material 1202 (e.g., a low-k dielectric material) may be formed over the first ILD material 204 by way of a vapor deposition technique. The second ILD material 1202 is then selectively exposed to a second etchant (e.g., $CF_4$, $CHF_3$, $C_4F_8$, HF, etc.) configured to selectively etch the second ILD material 1202 to form a second plurality of openings. A second metal material is formed in the second plurality of openings to form the via array and an overlying upper metal layer M4. In some embodiments, a chemical mechanical polishing (CMP) process may be used to remove excess of the second metal material from a top surface of the second ILD material 1202. In some embodiments, an upper metal layer M4 may be formed over the plurality of vias by way of a similar process. In other embodiments, one or more additional metal layers may be formed over the upper metal layer M4.

In some embodiments, the upper metal layer M4 may comprise one or more EWOD (electrowetting on dielectric) electrodes, 208a and 208b, and a signal output electrode 210. The EWOD electrodes, 208a and 208b, are configured to selectively generate electric fields that are configured to modify wetting properties of an overlying hydrophobic layer (e.g., 216) to control the flow of liquid within a micro-fluidic channel 218a. For example, the EWOD electrodes, 208a and 208b, may be configured to pump fluids in a manner that fills the sensing well 214. The signal output electrode 210 is configured to provide an output signal of the sensing device 202.

Figure 13:
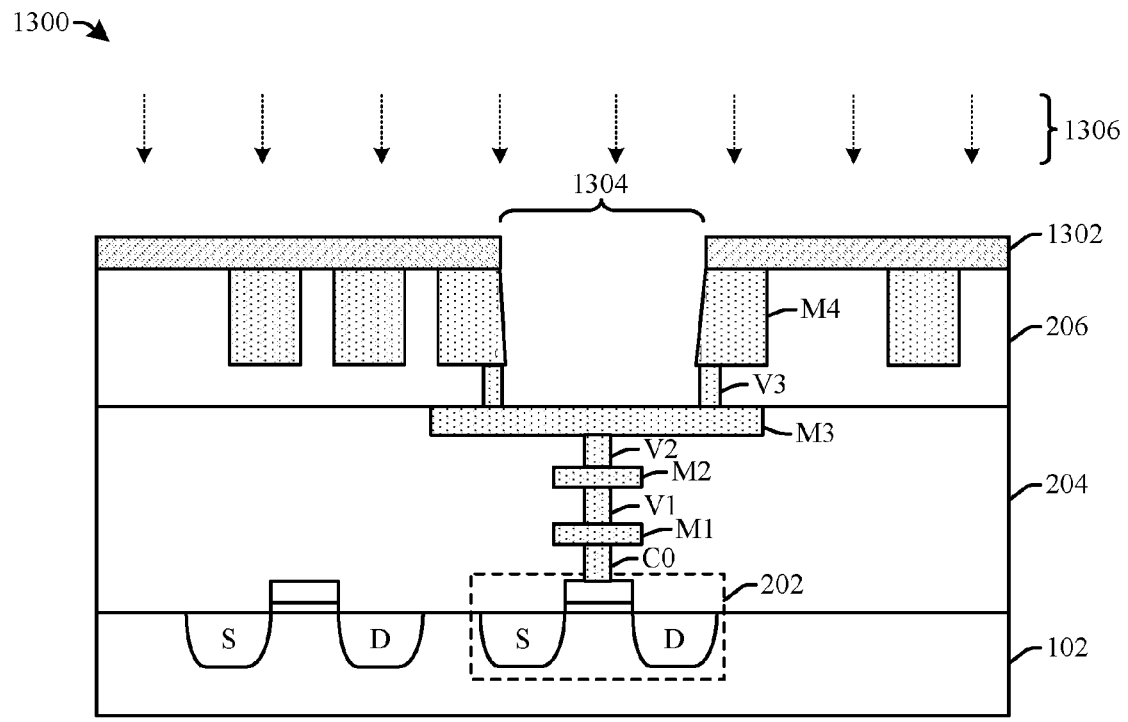

FIG. 13 illustrates some embodiments of a cross-sectional view 1300 of an integrated chip corresponding to act 912.

As shown in cross-sectional view 1300, a masking layer 1302 (e.g., photoresist or a hard mask) is selectively formed over the second ILD material 1202. The masking layer 1302 defines a position of a sensing well 1304 within the second ILD material 1202. The second ILD material 1202 is selectively exposed to a third etchant 1306 (e.g., $CF_4$, $CHF_3$, $C_4F_8$, HF, etc.) according to the masking layer 1302. The third etchant 1306 is configured to remove the second ILD material 1202 to form a sensing well 1304 within a top surface of the second ILD material 1202.

Figure 14:
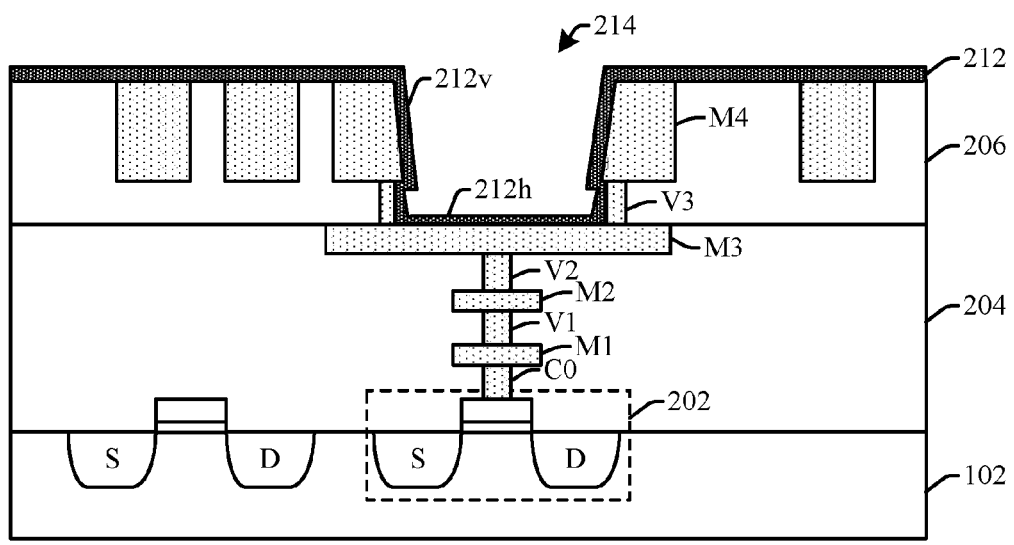

FIG. 14 illustrates some embodiments of a cross-sectional view 1400 of an integrated chip corresponding to act 914.

As shown in cross-sectional view 1400, a sensing enhancement layer 212 is deposited. The sensing enhancement layer 212 may be deposited by way of a vapor deposition process (e.g., PVD, ALD, CVD, PE-CVD). In some embodiments, the sensing enhancement layer 212 is deposited onto interior surfaces of the sensing well 214. In some embodiments, the sensing enhancement layer 212 may also be deposited along the top surface 206t of the second ILD material 206. In some embodiments, the sensing enhancement layer 212 may comprise a high-k dielectric material. For example, the sensing enhancement layer 212 may comprise one or more of silicon nitride ($Si_3N_4$), aluminum oxide ($Al_2O_3$), titanium oxide ($TiO_2$), hafnium oxide ($HfO_2$), tantalum pentoxide ($Ta_2O_5$), tin oxide (SnO), tin dioxide ($SnO_2$), $BaxSr_1$-$xTiO_3$ (BST).

Figure 15:
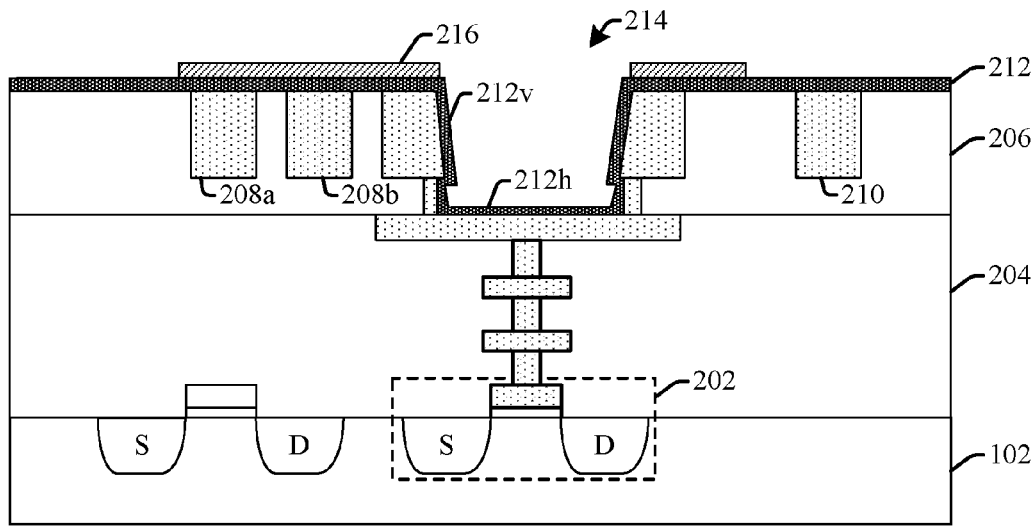

FIG. 15 illustrates some embodiments of a cross-sectional view 1500 of an integrated chip corresponding to act 916.

As shown in cross-sectional view 1500, a hydrophobic material is deposited to form a hydrophobic layer 216 over the sensing enhancement layer 212. In some embodiments, hydrophobic layer 216 may be disposed at a position overlying EWOD electrodes, 208a and 208b, within the upper metal wire layer. In some embodiments, the hydrophobic layer 216 may comprise a self assembled monolayer (SAM) or a teflon material.

Figure 16:
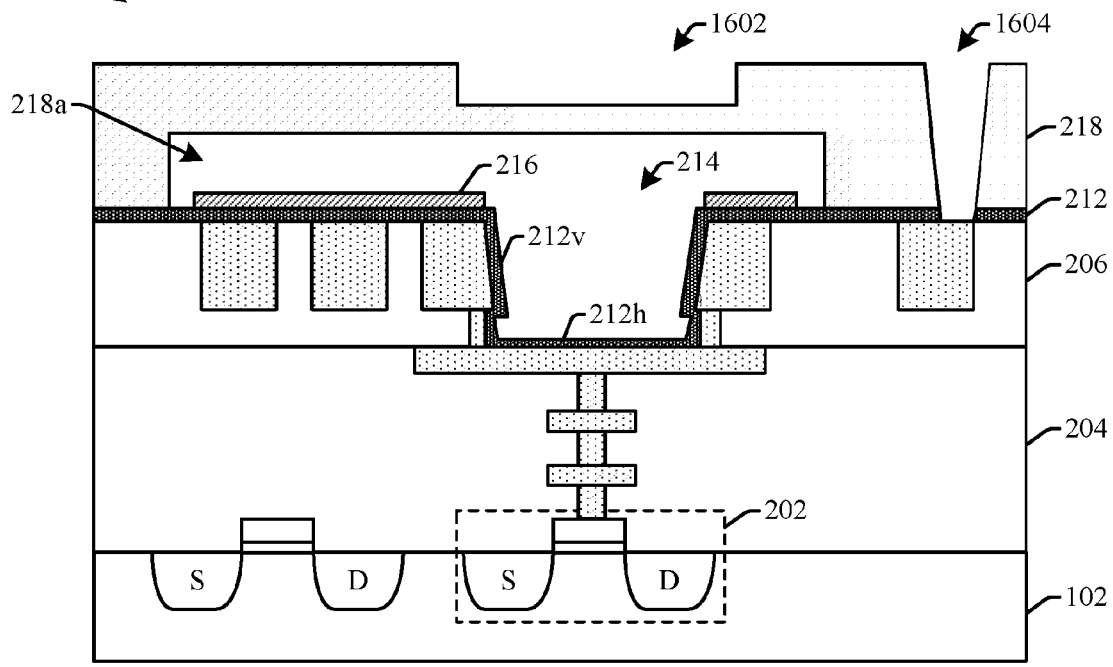

FIG. 16 illustrates some embodiments of a cross-sectional view 1600 of an integrated chip corresponding to act 916.

As shown in cross-sectional view 1600, a first capping structure 218 is formed over the second ILD material 206 to form a micro-fluidic channel 218a extending over the sensing well 214. The first capping structure 218 may be formed by depositing a polymer onto a molding substrate (not shown) and then curing the polymer. For example, PDMS may be spin-coated onto a molding substrate and then heated at an elevated temperature to form the first capping structure 218. The first capping structure 218 may be subsequently transferred from the molding structure to the second ILD material 206 to form the micro-fluidic channel 218a. In some embodiments, the first capping structure 218 may be bonded to the second ILD material 206 by way of an adhesive layer. In other embodiments, the first capping structure 218 may be bonded to the second ILD material 206 by way of a plasma activated bonding process, in which the PDMS and second ILD material 206 are exposed to a plasma (e.g., an oxygen plasma) and then brought into conformal contact.

Figure 17:
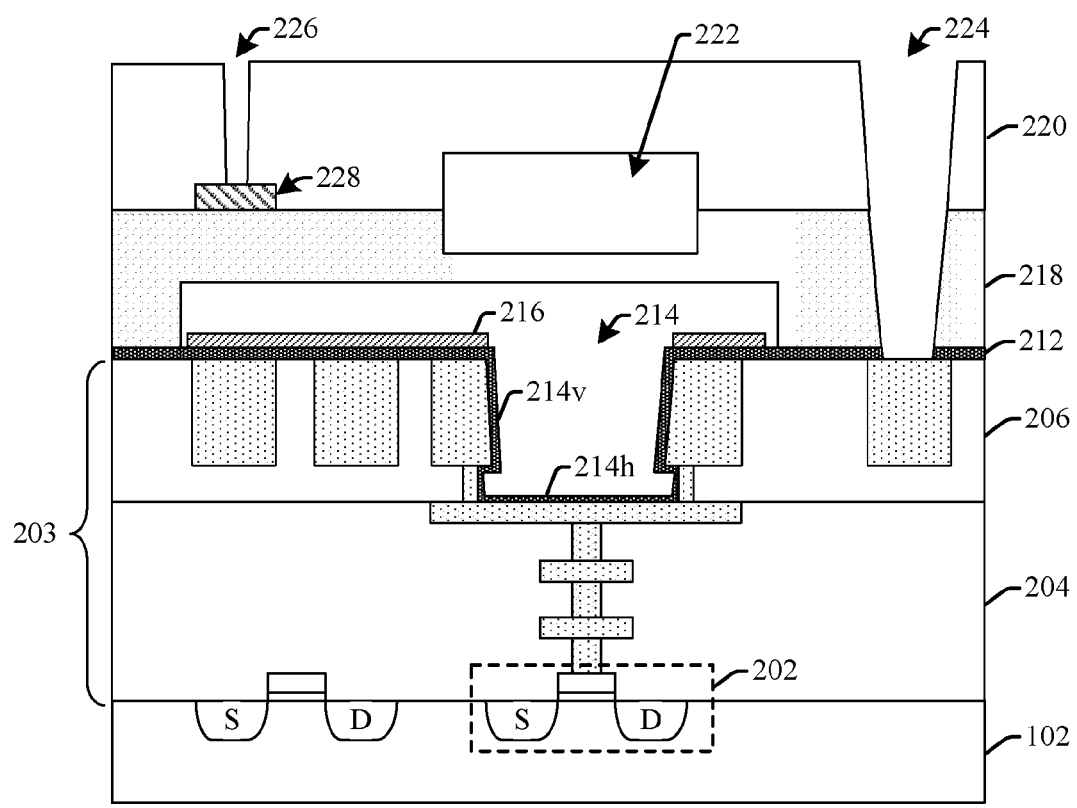

FIG. 17 illustrates some embodiments of a cross-sectional view 1700 of an integrated chip corresponding to act 918.

As shown in cross-sectional view 1700, a second capping structure 220 is formed over the first capping structure 218 to form a chamber 222 that can act as a valve or a peristaltic pump. The second capping structure 220 may be formed by selectively etching a substrate to form a second cavity and then bonding the etched substrate to the first capping structure 218. In various non-limiting examples, the second capping structure 220 may be bonded to the first capping structure 218 by way of an adhesion layer or a plasma activated bonding process. In some embodiments, a heating element 230 may be formed between the first capping structure 218 and the second capping structure 220.

In some embodiments, the first capping structure 218 and/or the second capping structure 220 may be subsequently etched after being bonding to form one or more openings. For example, a first etching process may be performed to form a first opening 224 that extends through the second capping structure 220 and the underlying first capping structure 218 to an underlying signal output electrode 210 within the upper metal layer M4. A second etching process may be performed to form a second opening 226 that exposes the temperature sensor 228 to an ambient environment, thereby allowing the temperature sensor 228 to measure a temperature of a liquid in the ambient environment. In some embodiments, the first and second etching processes may comprise one or more of the same etching processes and/or one or more different etching processes Therefore, the present disclosure relates to an integrated chip comprising an integrated bio-sensor having horizontal and vertical sensing surfaces.

In some embodiments, the present disclosure relates to an integrated chip. The integrated chip comprises a sensing device disposed within a substrate. A lower metal wire is over the substrate and electrically coupled to the sensing device. First and second metal vias are arranged on the lower metal wire at locations set back from sidewalls of the lower metal wire, and first and second upper metal wires respectively cover top surfaces of the first and second metal vias. A dielectric structure surrounds the lower metal wire, the first and second metal vias, and the first and second upper metal wires. A sensing well comprising sensing surfaces extends along an upper surface of the lower metal wire and along sidewalls of the first and second metal vias and the first and second upper metal wires.

In other embodiments, the present disclosure relates to an integrated chip. The integrated chip comprises a sensing device disposed within a substrate. A lower metal wire is electrically coupled to the sensing device. First and second metal vias are arranged on the lower metal wire at locations laterally offset from sidewalls of the lower metal wire, and first and second upper metal wires respectively over top surfaces of the first and second metal vias. A dielectric structure surrounds the lower metal wire, the first and second metal vias, and the first and second upper metal wires. The dielectric structure has an upper surface that is above lower surfaces of the first and second upper metal wires. A cavity extends along an upper surface of the lower metal wire and along sidewalls of the first and second metal vias and the first and second upper metal wires.

In yet other embodiments, the present disclosure relates to a method of forming an integrated bio-sensor. The method comprises forming a sensing device within a substrate, and forming a lower metal wire within a first ILD layer over the substrate. The lower metal wire is electrically connected to the sensing device. The method further comprises forming first and second metal vias within a second ILD layer. The first and second metal vias are arranged on the lower metal wire at locations laterally offset from sidewalls of the lower metal wire. The method further comprises forming a masking layer over the first and second metal vias, selectively etching the second ILD layer according to the masking layer to form a cavity over the lower metal wire and between the first and second metal vias, and removing the masking layer.

The foregoing outlines features of several embodiments so that those skilled in the art may better understand the aspects of the present disclosure. Those skilled in the art should appreciate that they may readily use the present disclosure as a basis for designing or modifying other processes and structures for carrying out the same purposes and/or achieving the same advantages of the embodiments introduced herein. Those skilled in the art should also realize that such equivalent constructions do not depart from the spirit and scope of the present disclosure, and that they may make various changes, substitutions, and alterations herein without departing from the spirit and scope of the present disclosure.

What is claimed is:

1. An integrated chip, comprising:
a sensing device disposed within a substrate;
a lower metal wire over the substrate and electrically coupled to the sensing device;
first and second metal vias arranged on the lower metal wire at locations set back from sidewalls of the lower metal wire;
first and second upper metal wires respectively covering the first and second metal vias;
a dielectric structure surrounding the lower metal wire, the first and second metal vias, and the first and second upper metal wires; and
a sensing well comprising sensing surfaces extending along an upper surface of the lower metal wire and along sidewalls of the first and second metal vias and the first and second upper metal wires.

2. The integrated chip of claim 1, wherein the first and second upper metal wires laterally extend past interior sidewalls of the first and second metal vias facing the sensing well.

3. The integrated chip of claim 1, wherein the first and second upper metal wires are electrically coupled to the first and second metal vias, respectively.

4. The integrated chip of claim 1, wherein the first and second upper metal wires protrude outward from opposing sidewalls of the dielectric structure into the sensing well.

5. The integrated chip of claim 1, wherein the dielectric structure has an upper surface that is above a lower surface of the first and second upper metal wires.

6. The integrated chip of claim 1, wherein the dielectric structure has an upper surface that is substantially co-planar with upper surfaces of the first and second upper metal wires.

7. The integrated chip of claim 1, wherein the dielectric structure separates the first upper metal wire from an adjacent upper metal wire surrounded by the dielectric structure.

8. The integrated chip of claim 1, wherein interior sidewalls of the first and second upper metal wire facing the sensing well have one or more arches.

9. The integrated chip of claim 1, further comprising:
one or more posts disposed within the sensing well and electrically coupled to the lower metal wire, wherein the one or more posts are arranged laterally between the first and second metal vias and comprise a metal via and an overlying metal wire.

10. An integrated chip, comprising:
a sensing device disposed within a substrate;
a lower metal wire electrically coupled to the sensing device;
first and second metal vias arranged on the lower metal wire at locations laterally offset from sidewalls of the lower metal wire;
first and second upper metal wires, which are respectively disposed directly above the first and second metal vias;
a dielectric structure surrounding the lower metal wire, the first and second metal vias, and the first and second upper metal wires, and having an upper surface that is above lower surfaces of the first and second upper metal wires; and
a cavity extending along an upper surface of the lower metal wire and along sidewalls of the first and second metal vias and the first and second upper metal wires.

11. The integrated chip of claim 10, wherein the first upper metal wire laterally straddles one or more sidewalls of the first metal via.

12. The integrated chip of claim 10, wherein the dielectric structure separates the first upper metal wire from an adjacent upper metal wire surrounded by the dielectric structure.

13. The integrated chip of claim 10, wherein the first and second upper metal wires are electrically coupled to the first and second metal vias, respectively.

14. The integrated chip of claim 10, wherein the first and second upper metal wires protrude outward from sidewalls of the dielectric structure into the cavity.

15. The integrated chip of claim 10, wherein the first and second metal vias and the first and second upper metal wires comprise copper.

16. The integrated chip of claim 10, wherein the dielectric structure laterally separates the first upper metal wire from an adjacent upper metal wire surrounded by the dielectric structure.

17. The integrated chip of claim 1, wherein the first metal via comprises a first sidewall facing the sensing well and having a first sidewall angle and a second sidewall facing away from the sensing well and having a second sidewall angle that is different than the first sidewall angle.

18. An integrated chip, comprising:
a lower metal wire surrounded by a first dielectric layer over a substrate and electrically coupled to a sensing device within the substrate;
a plurality of metal vias surrounded by a second dielectric layer and disposed on the lower metal wire at locations set back from sidewalls of the lower metal wire;
a plurality of upper metal wires surrounded by the second dielectric layer and covering tops of the plurality of metal vias, wherein the second dielectric layer extends from uppermost surfaces of the plurality of upper metal wires to lowermost surfaces of the plurality of metal vias; and
a sensing well comprising sensing surfaces extending along an upper surface of the lower metal wire and along sidewalls of the plurality of metal vias and the plurality of upper metal wires.

19. The integrated chip of claim 18, wherein the plurality of metal vias and the plurality of upper metal wires comprise copper.

20. The integrated chip of claim 18, wherein the plurality of metal vias respectively comprise a first sidewall facing the sensing well and having a first sidewall angle and a second sidewall facing away from the sensing well and having a second sidewall angle that is different than the first sidewall angle.

* * * * *